(12) United States Patent
Musso (10) Patent No.: US 7,098,206 B2
(45) Date of Patent: *Aug. 29, 2006

(54) PHARMACEUTICALLY ACTIVE MORPHOLINOL

(75) Inventor: David Lee Musso, Research Triangle Park, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 328 days.

This patent is subject to a terminal disclaimer.

(21) Appl. No.: 10/150,339

(22) Filed: May 17, 2002

(65) Prior Publication Data

US 2003/0064988 A1 Apr. 3, 2003

Related U.S. Application Data

(60) Continuation-in-part of application No. 09/886,391, filed on Jun. 22, 2001, now Pat. No. 6,391,875, which is a division of application No. 09/233,531, filed on Jan. 20, 1999, now Pat. No. 6,274,579.

(60) Provisional application No. 60/072,180, filed on Jan. 22, 1998.

(30) Foreign Application Priority Data

Jan. 21, 1998 (GB) .................................. 9801230

(51) Int. Cl.
  *A61K 31/535* (2006.01)
(52) U.S. Cl. .................................. 514/238.8
(58) Field of Classification Search ............. 514/238.8
  See application file for complete search history.

(56) References Cited

U.S. PATENT DOCUMENTS

| | | | |
|---|---|---|---|
| 3,536,809 A | 10/1970 | Applezweig |
| 3,598,123 A | 8/1971 | Zaffaroni |
| 3,622,675 A | 11/1971 | Koppe et al. |
| 3,630,200 A | 12/1971 | Higuchi |
| 3,819,706 A | 6/1974 | Mehta |
| 3,845,770 A | 11/1974 | Theeuwes et al. |
| 3,885,046 A | 5/1975 | Mehta |
| 3,916,899 A | 11/1975 | Theeuwes et al. |
| 3,960,927 A | 6/1976 | Metcalf et al. |
| 4,008,719 A | 2/1977 | Theeuwes et al. |
| 4,347,176 A | 8/1982 | Mehta |
| 4,347,177 A | 8/1982 | Phillips |
| 4,347,178 A | 8/1982 | Findlay et al. |
| 4,347,257 A | 8/1982 | Stern |
| 4,347,382 A | 8/1982 | Scharver |
| 4,355,179 A | 10/1982 | Findlay et al. |
| 4,356,165 A | 10/1982 | Findlay et al. |
| 4,393,078 A | 7/1983 | Peck |
| 4,425,363 A | 1/1984 | Stern |
| 4,435,449 A | 3/1984 | Stern |
| 4,438,138 A | 3/1984 | Stern |
| 4,507,323 A | 3/1985 | Stern |
| 4,571,395 A | 2/1986 | Peck |
| 4,656,026 A | 4/1987 | Coffman et al. |
| 4,687,660 A | 8/1987 | Baker et al. |
| 4,769,027 A | 9/1988 | Baker et al. |
| 4,798,826 A | 1/1989 | Peck |
| 4,835,147 A | 5/1989 | Roberts |
| 4,868,344 A | 9/1989 | Brown |
| 4,895,845 A | 1/1990 | Seed |
| 4,935,429 A | 6/1990 | Dackis et al. |
| 4,935,439 A | 6/1990 | Kashman et al. |
| RE33,994 E | 7/1992 | Baker et al. |
| 5,217,987 A | 6/1993 | Berger |
| 5,358,970 A | 10/1994 | Ruff et al. |
| 5,399,765 A | 3/1995 | Gao et al. |
| 5,427,798 A | 6/1995 | Ludwig et al. |
| 5,447,948 A | 9/1995 | Seibyl |
| 5,512,593 A | 4/1996 | Dante |
| 5,541,231 A | 7/1996 | Ruff et al. |
| 5,648,347 A | 7/1997 | Mehta et al. |
| 5,731,000 A | 3/1998 | Ruff et al. |
| 5,753,712 A | 5/1998 | Pinsker |
| 5,763,493 A | 6/1998 | Ruff et al. |
| 6,274,579 B1 | 8/2001 | Morgan et al. |
| 6,337,328 B1 | 1/2002 | Fang et al. |
| 6,342,496 B1 | 1/2002 | Jerussi et al. |
| 6,391,875 B1 | 5/2002 | Morgan et al. |
| 2002/0052340 A1 | 5/2002 | Jerussie et al. |
| 2002/0052341 A1 | 5/2002 | Fang et al. |

FOREIGN PATENT DOCUMENTS

| | | |
|---|---|---|
| CA | 977777 | 11/1975 |
| CA | 977778 | 11/1975 |
| EP | 0 118 036 | 9/1984 |
| EP | 0 170 430 A1 | 2/1986 |
| EP | 0 171 227 | 2/1986 |
| EP | 0 467 488 | 1/1992 |

(Continued)

OTHER PUBLICATIONS

Golden et al., "Bupropion in Depression," Arch. Gen Psychiatry, vol. 45, Feb. 1988.

(Continued)

*Primary Examiner*—Vickie Kim
(74) *Attorney, Agent, or Firm*—Bonnie L. Deppenbrock (57) ABSTRACT

Disclosed is the compound (+)-(2S,3S)-2-(3-chlorophenyl)-3,5,5-trimethyl-2-morpholinol and pharmaceutically acceptable salts and solvates thereof, pharmaceutical compositions comprising them, and processes for their preparation and use; also disclosed is a method of treating depression, attention deficit hyperactivity disorder (ADHD), obesity, migraine, pain, sexual dysfunction, Parkinson's disease, Alzheimer's disease, or addiction to cocaine or nicotine-containing (especially tobacco) products using such compound, salts, solvates or compositions.

5 Claims, 6 Drawing Sheets

FOREIGN PATENT DOCUMENTS

| | | |
|---|---|---|
| JP | 63-91352 | 4/1988 |
| WO | 91/11184 | 8/1991 |
| WO | 92/18489 | 10/1992 |
| WO | 92/19226 | 11/1992 |
| WO | 93/21917 | 11/1993 |
| WO | 94/04138 | 3/1994 |
| WO | 94/20100 | 9/1994 |
| WO | 95/03791 | 2/1995 |
| WO | 95/22324 | 8/1995 |
| WO | 96/39133 | 12/1996 |
| WO | 97/29735 | 8/1997 |
| WO | 98/50044 | 11/1998 |
| WO | 99/37305 | 7/1999 |
| WO | 01/62257 | 8/2001 |

OTHER PUBLICATIONS

Laizure, et al., "Pharmacokinetics of bupropion and its major basic metabolites in normal subjects after a single dose," *Clin. Pharm. Ther.*, 1985 (38), pp. 586-589.

Suckow, et al., "Enantiomeric Determination of the Phenylmorpholinol Metabolite of Bupropion in Human Plasma Using Coupled Achiral-Chiral Liquid Chromatography," *Biomedical Chromatography*, 1997, vol. 11, pp. 174-179.

Welch, et al., "Phmaracological significance of the species difference in bupropion metabolism," *Xenobiotica*, 1987, vol. 17, No. 3, pp. 287-298.

Suckow, et al., "Pharmacokinetics of Bupropion and Metabolites in Plasma and Brain of Rats, Mice, and Guinea Pigs," *The American Society for Pharmacology and Experimental Therapeutics*, 1986, vol. 14, No. 6, pp. 692-697.

Posner, J., et al., "The Disposition of Bupropion and Its Metabolites in Healthy Male Volunteers After—and Multiple Doses," *Eur. J. Clin. Pharmacol.*, 1985, vol. 29, pp. 97-103.

Ascher, J.A., et al., "Bupropion: A Review of its Mechanism of Antidepressant Activity," *J. Cling. Psych.*, 1995, vol. 56, pp. 395-401.

Martin et al., "Antidepressant Profile of Bupropion and three Metabolites in Mice," *Pharmacopsychiatry*, 1990, vol. 23, pp. 187-194.

Eisman, et al., "The Isolation and Identification of Some Basic Urinary Metabolites of Bupropion-HCL in Man," *Pharmacologist*, 1979, vol. 21, p. 191.

Cooper et al., "Behavioral and Biochemical Effects of the Antidepressant, Bupropion (Wellbutrin): Evidence for Selective Blockade of Dopamine Uptake in Vivo," *The Journal of Pharmacology and Experimental Therapeutics*, 1980, vol. 215, No. 1.

Ferris et al., "Some Neurochemical Properties of a New Antidepressant, Bupropion Hydrochloride (Wellbutrin)," *Drug Development Research*, 1981, vol. 1, pp. 21-35.

Maxwell, et al., "Bupropion," *Pharmacol & Biochem Properties Drug Substances* (M E Goldberg, Ed), Am Pharm Assoc. Pub., Washington, 1981, vol. 3, pp. 1-55.

Findlay, et al., "Pharmacokinetics of Bupropion, a Novel Antidepressant Agent, Following Oral Administration to Healthy Subjects," *European Journal of Clinical Pharmacology*, 1981, vol. 21, pp. 127-135.

Butz, et al., "Radioimmunoassay and Pharmacokinetic Profile of Bupropion in the Dog," *The Journal of Pharmacology and Experimental Therapeutics*, 1981, vol. 217, No. 3.

Ferris et al., "Bupropion: A New Antidepressant Drug, The Mechanism of Action of Which is Not associated with Down-Regulation of Postsynaptic β-Adrenergic, Serotonergic (5-HT$_2$), α2-Adrenergic, Imipramine and Dopaminergic Receptors in Brain," *Neuropharmacology*, 1983, vol. 22, No. 11, pp. 1257-1267.

Mehta, "The Chemistry of Bupropion," *J. Clinical Psychiatry*, May 1983, 44:5 (Sec. 2).

Schroeder, David, "Metabolism and Kinetics of Bupropion," *J. Clinical Psychiatry*, May 1983, 44:5 (Sec. 2).

Lai, et al., "Clinical Pharmacokinetics of Bupropion: A Reivew," *J. Clinical Psychiatry*, May 1983, 44:5 (Sec. 2).

Cooper et al., "Determination of Bupropion nd Its Major Basic Metabolites in Plasma by Liquid Chromatography with Dual-Wavelength Ultraviolet Detection," *Journal of Pharmaceutical Sciences*, Aug. 1984, vol. 73, No. 8.

Laizure et al., "Stability of Bupropion and its Major Metabolites in Human Plasma," *Therapeuytic Drug Monitoring*, 1985, vol. 7, pp. 447-450.

Cooper, et al., "Bupropion: Possible Rose of Major Metabolites in Mode of Action," *Clin. Pharmacol. Ther.*, Feb. 1985, vol. 37, No. 2.

DeVane, et al., "The Effect of Experimentally-Induced Renal Failure on Accumulation of Bupropion and its major basic metabolites in plasma and brian of guinea pigs," *Psychopharmacology*, 1986, vol. 89, pp. 404-408.

Perumal, et al., "Effect of Plasma from Patients Contianing Bupropion and its Metabolites on the Uptake of Norepinephrine," *Neuropharmacology*, 1986, vol. 25, No. 22, pp. 199-202.

Thomas Smith et al., "Brain regional [$^3$H]flunitrazepam binding in rats chronically treated with bupropion or B.W.306U," *Brain Research*, 1986, 367, pp. 385-389.

Ferris et al., "Mechanism of Antidepressant Activity of Bupropion," *J Clin Psychiatry Monograph*, 1993, vol. 11, pp. 2-14.

Musso, et al., Synthesis and Evaluation of the Antidepressant Activity of the Enantiomers of Bupropion, *Chirality*, 1993, vol. 5, pp. 495-500.

Hsyu, et al., "Pharmacokinetics of Bupropion and its Metabolites in Cigarette Smokers versus Nonsmokers," *J. Clin. Pharmacol.*, 1997, vol. 37, pp. 737-743.

Modell, et al., "Comparative sexual side effects of bupropion, fluoxetine, paroxetine, and sertraline," *Clinical Pharmacology & Therapeutics*, 1996, vol. 61, No. 4.

Cooper, et al., "Evidence that the Acute Behavioral and Electrophysiolgical Effects of Bupropion (Wellbutrin) are Mediated by a Noradrenergic Mechanism," *Neuropsychopharmacology*, 1994, vol. 11, No. 2, 99133-141.

Bannon et al., 1998, "Broad-spectrum, non-opoid analgesic activity by selective modulation of neuronal nicotinic acetylchroline receptors," *Science*, vol. 279, pp. 77-81.

Bischoff et al., 1984, "Affinity changes of rat striatal dopamine receptor in vivo after acute bupropion treatment," *Eur. J. Pharmaco.*, vol. 104, pp. 173-176.

Blondel-Hill et al., 1993, "Treatment of the chronic fatigue syndrome," *Drugs*, vol. 46, No. 4, pp. 639-651.

Borowski, T.B., et al., 1993, Amphetamine and antidepressant drug effects of GABA—and NMDA—related seizures, *Brain Res. Bull.*, vol. 30, pp. 607-610.

Calabrese, J.R. et al., 1991, "Treatment of depression," *Primary Care*, vol. 18, No. 2, pp. 421-433.

Castaldi, G. et al., 1987, "Tataric acid and efficient chiral auxillary: new asymmetric synthesis of 2-alkyl-2-arylacetic acids," *J. Org. Chem.*, vol. 52, p. 3018.

Castello, R.A., and Mattons, A.M., *J. Pharm. Sci.*, vol. 51, No. 2, pp. 106-108 (1962).

Charney, D.S. et al., 1983, "Monoamine receptor sensitivity and depression: clinical studies of antidepressant effects on serotonin and noradrenergic function," *Psychopharmac. Bull*, 19(3)p. 490.

Clay et al., 1988, "Clinical and neuropsychological effects of the novel antidepressant bupropion," *Psychopharma. Bull.*, 24(1), pp. 143-148.

Conners, K.C. et al., 1996, "Bupropion hydrochloride in attention deficit disorder with hyperactivity," *J. Am. Acad. Child Adolesc. Psychiatr.*, 34(10), pp. 1314-1321.

Cooke, C.E., 1997, Therapeutic advances in the treatment of cigarette addiction, *J. Pharmacy Practice*, 10(5) pp. 329-337.

Cooper, T.B. et al., Analytical psychopharmacology: NY State Psychiatric Institute, pp. 1-3, 1988.

Coutts, R.T. & Baker, G.B., 1989, "Implications of chirality and geometeric isomerisms in some psychoactive drugs and their metabolites," *Chirality*, 1, pp. 99-120.

Crenshaw et al., 1987, "Pharmacological modification of psychosexual dysfunction," *J. Sex. Marital Ther.*, 13(4), pp. 239-252.

Cusack, B. et al., 1994, "Binding of antidepressants to human brain receptors: focus on newer generation compounds," *Psychopharmacol.*, 114, pp. 559-565.

Davidson et al., 1994, "Bupropion in chronic low back pain," *J. Clin. Psychiatry*, 55(8), p. 362.

Dilsaver, S.C. et al., 1992, "The efficacy of bupropion in winter depression: results of an open trial," *J. Clin. Psychiatry*, 53(7), pp. 252-255.

Eliel, E.L., 1962, *Stereochemistry of Carbon Compounds*, McGraw-Hill, NY.

Ferris, R.M. et al., 1983, "Studies of bupropion's mechanism of antidepressant activity," *J. Clin. Psychiatry*, 44(5), pp. 74-78.

Ferry, L.H. et al., 1992, "Enhancement of smoking cessation using the anti-depressant bupropion-hydrochloride," (abstract) Curculation 86:671.

Ferry, L.H. et al., 1994, "Efficacy of bupropion for smoking cessation in non-depressed smokers," *J. Addict*, Dis. 13:A9.

Fisher, R.S., 1989, "Animal models of epilepsies," *Brain Res. Reviews*, 14:245-278.

Foote et al., 1984, "Proconvulsant effect of morphine on seizures induced by pentlyenetetrazol in the rat," 105:179-184.

Garland et al., 1998, "Pharmacotherapy of adolescent attention deficit hyperactivity disorder: challenges, choices and caveats," *J. Psychopharmacology*, 12(4):385-395.

Goetz et al., 1984, "Bupropion in Parkinson's Disease," 34:1092-4.

Goodnick, P.J., 1994, "Pharmacokinetic optimisaton of therapy with newer antidepressants," *Clin. Pharmacokinet*, 27(4):307-330.

Goodnick, P.J. & Sandoval, R., 1993, "Psychotropic treatment of depression: results of an open trial," *J. Clin. Psych.* 54(1):13-20.

Green, A.R. & Murray, T.K., 1989, "A simple intravenous infusion method in rodents for determining potency of anticonvulsants acting through GABAergic mechanisms," *J. Pharm. Pharmacol.* 41:879-880.

Grimes et al., 1996, "Spontaneous orgasm with the combined use of bupropion and serttaline," *Soc. Biol. Psych.* 40:1184-1185.

*Handbook of Pharmaceutical Excipients*, 2nd ed., Wade and Willer eds, pp. 257-259 (1994).

Hsyu, P.H. et al., Nov. 10, 1997 Chemical Abstacts 127(19): Abstract No. 257089; Columbus, Ohio.

Janowsky, A., et al., *J. Neurochem.* 45:1272-1276 (1986).

Kelley, J.K. et al., 1996, "(2S,3S,5R)-2-(3,5,-difluorophenyl)-3,5,-dimethyl-2-morpholinol: a novel antidepressant agent and selective inhibitor of norepiniphrine uptake," *J. Med. Chem.* 39:347-349.

Ketter, T.A. et al., 1995, "Carbamazepine but not valproate induces bupropion metabolism," *J. Clin. Psychopharmacol.* 15(5):327-333.

Lief, H.I., 1996, "Bupropion treatment of depression to assist smoke cessation," *Am. J. Psychiatry* 153(3):442.

Little, K.Y. et al., 1993, "[$^{125}$I]RTI-55 binding to cocaine-sensitive dopaminergic and serotonergic uptake sites in the human brain," *J. Neurochem.* 61:1996-2006.

McNamee et al., 1986, "Stimulation of substrate oxidation in rat hepatic mitochondria following pretreatment with apetite modifying drugs," *J. Pharm. Pharmacol.* 37:147.

Merskey, H., 1965, "The effect of chronic pain upon the response to noxious stimuli by psychiatric patients," *J. Psychosom. Res.*, 8:405-419.

Mitchell, G.F. et al., 1989, "Effect of bupropion on chocolate craving," *Am. J. Psychiatry*, 146(1):119-120.

Mitchell, G.F. et al., 1989, "Dr. Mitchell and associates reply," *Am. J. Psychiatry*, 146(8):1089.

Moisset, B. et al., *Brain Res.*, 92:157-164 (1975).

Moret, C. & Brile, M., 1988, "Sensitizing of the response of 5-HT autoreceptors to drugs modifying synaptic availablity of 5-HT", 27(1):43-49.

Musso et al., 1997, "Synthesis and Evaluation of the Anticonvulsant Activity of a Series of 2-Amino-Phenyl-1-Propanols Derived from the Metabolites of the Antidepressant Bupropion," *Bioorganic & Medical Chemistry Letters*, vol. 7 No. 1, pp. 1-6, 1997.

*Neurology*, Official-Journal of American Academy of Neurology, Aug. 1984, vol. 34, No. 8.

Nomikos, et al., 1992, "Effects of chronic bupropion on interstitial concentrations of dopamine in rat nucleus accumbens and striatum," *Neuropsychopharmacology* 7(1):7-14.

Nutt, D.J. et al., 1981, "Studies on the postietal rise in seizure threshold," *Eur. J. Phamacol.*, 71:287-295.

Nutt et al., 1980, "On the measurement in rats of the convulsant effect of drugs and the changes which follow electroconvulsive shock," *Neuropharmacology* 19:1017-1023.

Olsen et al., 1985, "Benzodiazepine/γ-aminobutyric acid receptor deficit in the midbrain of the seizure-susceptible gerbil," *PNAS USA* 82:6701-6705.

Pearlstein et al., 1997, "Comparison of fluoxetine, bupropion, and placebo in the treatment of premenstrual dysphoric disorder," *J. Clin. Psychopharmacol.* 17(4):261-266.

Physicians Desk Reference®, 1998, pp. 1120-11274.

Popli, A.P., et al., 1994, "Antidepressant-associated seizures," *J. Clin. Psych.* 55(6):267.

Popli, A., et al., 1995, "Bupropion and anticonvulsant drug interactions," *Annals of Clin. Psychiatr.* 7(2):99-101.

Potter, W.Z. & Janji, H.K., 1990, "Antidepressants, metabolites, and apparent drug resistance," *Clin. Neuropharmacol.*, 13(1):S45-S53.

Remingtons: *The Practice of the Science and Pharmacy*, 19th ed., Gennaro, eds., p. 1625 (1995).

Rose, J.E., 1996, "Nicotine addiction and treatment," *Annu. Rev. Med.*, 47:493-507.

Rosenstein, D.L., et al., 1993, "Seizure associated with antidepressants: a review," *J. Clin. Psychiatry* 54(8): 289-299.

Rudorfer, M.V. et al., 1994, "Comparative tolerability profiles of the newer versus older antidepressants," *Drug Safety* 10(1):18-46.

Schroeder, D.H., 1979, "The isolation and identification of some basic urinary metabolites of bupropion—HCL in man," *The Pharmacologist* 21(3):191.

Scrip Bupropion Sustained Release (SR) for Smoking Cessation, Dec. 18, 1996.

Scrip Itraconazole for pulse dosing of onychomycosis, Dec. 18, 1996.

Scrip's New Product Review, No. 50 Bupropion, PJB Publications: United Kingdom, Aug. 1990.

Stathis, M. et al., 1995, "Rate of binding of various inhibitors at the dopamine transporter in vivo," *Psychopharmacol.*, 119:376-384.

Storrow, A.B., 1994, "Bupropion overdose and seizure," *Am. J. Emerg. Med.*, 12:183-184.

Sulser, F., 1983, "Molecular mehcanisms in antidepressant action," *Psychopharmacol. Bull.* 19(3):300.

Sweet, R.A., et al., 1995, "Pharmacokinetics of single-and multiple-dose bupropion in elderly patients with depression," *J. Clin. Pharmacol.*, 35:876-884.

Testa, B. and Trager, W.F., 1990, "Racemates Versus Enantiomers in Drug Development: Dogmatism or Pragmatism?" *Chirality* 2:129-133.

Vassout, A., et al., 1993, "Regulation of dopamine receptors by bupropion comparison with antidepressants and CNS stimulants," *J. Rceptor Res.*, 13(1-4):341-354.

Ward, N.G., 1990, *The Management of Pain*, Second Edition, vol. 1, chapter 18 (eds.) Bonica, J.J. pp. 310-319.

Ward, R., et al., 1971, Asymmetric audiogenic seizures in mice: a possible analogue of focal epilepsy, *Brian Res.*, 31:207-210.

Wilen, S.H., 1972, *Tables of Resolving Agents in Optical Resolutions*, Univ. of Notre Dame Press, Notre Dame, IN.

Wright et al., 1985, "Bupropion in the long-term treament of cyclic mood disorders: mood stabilizing effects," *J. Clin. Psych.* 46(1):22-25.

Zarrindast et al., 1988, "Anoretic and behavioral effects of bupropion," *Gen. Pharmacology*, 19(2):201-204.

Boswell, G. Evan et al., "Synthesis and Anti-tetrabenazine Activity of C-3 Analogues of Dimethyl-2-phenylmorpholines," J. Heterocyclic Chem., vol. 33, pp. 33-39 (Jan.-Feb. 1996).

Boswell, G. Evan et al., "Synthesis, Stereochemistry and Anti-tetrabenazine Activity of Bicyclo Analogues 2-phenylmorpholines," J. Heterocyclic Chem., vol. 34, pp. 1813-1820 (Nov.-Dec. 1997).

PHARMACEUTICALLY ACTIVE MORPHOLINOL

This application is a continuation-in-part of U.S. Ser. No. 09/886,391 filed 22 Jun. 2001, now U.S. Pat. No. 6,391,875, which is a divisional application of U.S. Ser. No. 09/233,531, filed 20 Jan. 1999, now U.S. Pat. No. 6,274,579 and claims the benefit of Provisional Application No. 60/072,180, filed Jan. 22, 1998.

This invention relates to an optically pure morpholinol, salts and solvates thereof, pharmaceutical formulations containing them and processes for their preparation and use.

BACKGROUND OF THE INVENTION

Bupropion hydrochloride, (±)-1-(3-chlorophenyl)-2-[(1,1-dimethylethyl)amino]-1-propanone hydrochloride, is the active ingredient of Wellbutrin® which is marketed in the United States for the treatment of depression. It is also the active ingredient of Zyban® which is marketed in the United States as an aid to smoking cessation. Bupropion is a relatively weak inhibitor of the neuronal uptake of noradrenaline (NA), serotonin and dopamine (DA), and does not inhibit monoamine oxidase. While the mechanism of action of bupropion, as with other antidepressants, is unknown, it is presumed that this action is mediated by noradrenergic and/or dopaminergic mechanisms. Available evidence suggests that Wellbutrin® is a selective inhibitor of noradrenaline (NA) at doses that are predictive of antidepressant activity in animal models. See Ascher, J. A., et al., Bupropion: A Review of its Mechanism of Antidepressant Activity. *Journal of Clinical Psychiatry*, 56: p. 395–401, 1995.

Bupropion HCl

Bupropion is extensively metabolized in man as well as laboratory animals. Urinary and plasma metabolites include biotransformation products formed via hydroxylation of the tert-butyl group and/or reduction of the carbonyl group of bupropion. Four basic metabolites have been identified. They are the erythro- and threo-amino alcohols of bupropion, the erythro-amino diol of bupropion, and a morpholinol metabolite. These metabolites of bupropion are pharmacologically active, but their potency and toxicity relative to bupropion have not been fully characterized. Because the plasma concentrations of the metabolites are higher than those of bupropion, they may be of clinical importance.

The morpholinol metabolite (+/−)-(2R*,3R*)-2-(3-chlorophenyl)-3,5,5-trimethyl-2-morpholinol hydrochloride is believed to be formed from hydroxylation of the tert-butyl group of bupropion.

Morpholinol Metabolite of Bupropion HCl

SUMMARY OF THE INVENTION

It has now surprisingly been discovered that despite the (−) form of the morpholinol metabolite predominating significantly in human plasma samples, it is the (+) enantiomer, (+)-(2S,3S)-2-(3-chlorophenyl)-3,5,5-trimethyl-2-morpholinol in which the activity resides.

Thus the present invention provides, in one aspect, the compound of formula (I), (+)-(2S,3S)-2-(3-chlorophenyl)-3,5,5-trimethyl-2-morpholinol or pharmaceutically acceptable salts and solvates thereof.

Another aspect of the invention is pharmaceutical compositions comprising a compound of formula (I) or pharmaceutically acceptable salts and solvates thereof together with one or more pharmaceutically acceptable carriers, diluents or excipients.

A further aspect of the present invention is the use of a compound of formula (I) or pharmaceutically acceptable salts and solvates thereof in therapy.

Yet another aspect of the invention provides methods of treating depression, attention deficit hyperactivity disorder (ADHD), obesity, migraine, pain, sexual dysfunction, Parkinson's disease, Alzheimer's disease, or addiction to cocaine or nicotine-containing (especially tobacco) products in a mammal (human or animal subject) comprising the administration to said subject of an effective amount of a compound of formula (I) or pharmaceutically acceptable salts and solvates thereof or pharmaceutical compositions thereof.

Yet another aspect of the present invention is the use of the compound of formula (I) or pharmaceutically acceptable salts and solvates thereof or pharmaceutical compositions thereof in the preparation of a medicament for the treatment of depression, attention deficit hyperactivity disorder (ADHD), obesity, migraine, pain, sexual dysfunction, Parkinson's disease, Alzheimer's disease, addiction to cocaine or nicotine-containing (especially tobacco) products.

DETAILED DESCRIPTION OF THE INVENTION

It will be appreciated that references herein to "treatment" extend to prophylaxis, prevention of recurrence and suppression or amelioration of symptoms (whether mild, moderate or severe) as well as the treatment of established conditions.

As used herein, the term "method of treating depression" includes treatment of a major depressive disorder (MDD), bipolar depression (type I and II), and depression with a typical features (e.g. lethargy, over-eating/obesity, hypersomnia). In such treatments, accompanying treatment (alleviation) of depression-related anxiety symptoms is also contemplated. Treatment of major (unipolar) depression is of particular interest. In the treatment of depressive episodes in bipolar disorder, the extent or severity of activation of mania/hypermania (switching) is expected to be improved relative to known antidepressants, especially those of the SSRI-class.

As used herein, the term "a method for treating obesity" means both partial and complete alleviation of the condition. Thus, as well as alleviation of obesity, this will also include reducing the degree of severity of obesity. Included within this term is the prevention of weight gain (avoiding weight gain and attenuating the amount of weight gain in a susceptible subject), the production of weight loss, or maintaining weight loss (preventing re-gain of weight lost as a result of treatment with the compound of formula (I) or as a result of diet or exercise in the absence of treatment with a compound of formula (I)). The method may be employed even if the subject being treated is not obese or overweight according to clinical measures. The method may be employed pre-emptively in those subjects at risk of obesity e.g. in individuals attempting to quit smoking, diabetics, or those individuals being treated with certain drugs (including antidiabetics and antidepressants) which are known or suspected to promote weight gain.

As used herein the term "a method for treating pain" encompasses in particular the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

As used herein, the term "method of treating sexual dysfunction" encompasses prevention of, or treatment relief from, sexual dysfunction or one or more symptoms of sexual dysfunction. The term "sexual dysfunction" as used herein principally encompasses psychosexual dysfunction. Examples of psychosexual dysfunction include, but are not limited to, inhibited sexual desire (low libido), inhibited sexual arousal or excitement, orgasm dysfunction, inhibited female orgasm and inhibited male orgasm. Particular examples of more specifically defined disorders include hypoactive sexual desire disorder (HSDD) and female sexual desire disorder (FSDD). Of particular note is the alleviation of sexual dysfunction side-effects induced by treatment with antidepressants of the SSRI-class.

As used herein, the term "method of treating Parkinson's disease" means relief from the symptoms of Parkinson's disease which include, but are not limited to, locomotor deficits and/or motor disability, including slowly increasing disability in purposeful movement, tremors, bradykinesia, hyperkinesia (moderate and severe), akinesia, rigidity, disturbance of balance and co-ordination, and a disturbance of posture.

As used herein, the term "treatment of addiction to nicotine-containing products" includes both partial and complete alleviation of addiction. Thus, in respect of tobacco products, as well as the cessation of the activity, for example smoking, this will also include reducing the level or frequency of such activity e.g. reduction of the number of cigarettes smoked in a given period. In respect of other nicotine-containing products, treatment will also involve both cessation of, and a reduction in the level of, usage of such products. The term "treatment of addiction to cocaine products" has an analogous meaning.

Preparation

The compound of formula (I) or pharmaceutically acceptable salts and solvates thereof may be prepared by first synthesizing the racemate of the morpholinol metabolite of bupropion and subsequently separating the (+) and (−) enantiomers of the racemate via HPLC.

The racemate of the morpholinol metabolite of bupropion hydrochloride ((+/−)-(2R*,3R*)-2-(3-chlorophenyl)-3,5,5-trimethyl-2-morpholinol hydrochloride) may be synthesized by the following process. To 3'-chloropropiophenone (10.0 g, 0.06 mol) in dioxane (50 mL) was added a solution of dioxane dibromide (14.9 g, 0.06 mol) in dioxane (50 mL). The reaction mixture was stirred for 2 h at ambient temperature and poured into a mixture of ice and water (500 mL). The mixture was extracted several times with methylene chloride. The combined extracts were dried ($Na_2SO_4$) and concentrated in vacuo to give 14.8 g (85%) of 2-bromo- 3'-chloropropiophenone as a pale yellow oil. This was used without further purification. NMR (300 Mhz, CDCl$_3$); δ 7.99 (m, 1H), 7.90 (d, 1H), 7.57 (d, 1H), 7.44 (t, 1H), 5.22 (q, 1H), 1.91 (t, 3H).

To a solution of 2-bromo-3'-chloropropiophenone (19.3 g, 0.08 mol) in MeOH (100 mL) was added dropwise a solution of 2-amino-2-methyl-1-propanol (27.8 g, 0.31 mol) in methanol (200 mL) at ambient temperature. The mixture was stirred for 18 h and concentrated in vacuo. The residue was partitioned between water and diethyl ether. The combined organic phase was extracted with 10% aqueous hydrogen chloride. The combined aqueous acid extracts were chilled in an ice bath and made basic with 40% aqueous sodium hydroxide. The mixture was extracted with diethyl ether, the combined diethyl ether extracts were washed with water and saturated sodium chloride solution, dried (K$_2$CO$_3$) and concentrated in vacuo to give 15.0 g (75%) of (+/−)-(2R*,3R*)-2-(3-chlorophenyl)-3,5,5-trimethyl-2-morpholinol as an off-white solid.

(+/−)-(2R*,3R*)-2-(3-chlorophenyl)-3,5,5-trimethyl-2-morpholinol may be converted to (+/−)-(2R*,3R*)-2-(3-chlorophenyl)-3,5,5-trimethyl-2-morpholinol hydrochloride by the following process. A 6.0 g sample was dissolved in diethyl ether, chilled in an ice bath and ethereal hydrogen chloride added until the mixture was acidic. The resulting solid was filtered and recrystallized from ethanol/diethyl ether/ethereal hydrogen chloride mixtures to give 4.93 g of (+/−)-(2R*,3R*)-2-(3-chlorophenyl)-3,5,5-trimethyl-2-morpholinol hydrochloride as a white solid: m.p. 202–203° C. NMR (80 Mhz, DMSO-d$_6$); δ 10.9 (br, 1H), 8.85 (br, 1H), 7.60–7.41 (m, 5H), 4.04 (d, 1H), 3.50 (d, 1H), 3.37 (br s, 1H), 1.58 (s, 3H), 1.34 (s, 3H), 1.03 (d, 3H). Anal. Calcd for C$_{13}$H$_{19}$Cl$_2$NO$_2$: C, 53.43; H, 6.55; N, 4.79. Found: C, 53.54; H, 6.58; N, 4.75.

(+/−)-(2R*,3R*)-2-(3-chlorophenyl)-3,5,5-trimethyl-2-morpholinol hydrochloride may be converted back to its free base by the following process. A 3.0 g sample of (+/−)-(2R*,3R*)-2-(3-chlorophenyl)-3,5,5-trimethyl-2-morpholinol hydrochloride was dissolved in water (100 mL) and diethyl ether was added (200 mL). The mixture was chilled in an ice bath and the pH was adjusted to >10 with 1.0N aqueous sodium hydroxide. After stirring for 30 min., the phases were separated and the aqueous phase was extracted with diethyl ether. The combined diethyl ether extracts were dried (Na$_2$SO$_4$) and concentrated in vacuo to give 2.6 g of (+/−)-(2R*,3R*)-2-(3-chlorophenyl)-3,5,5-trimethyl-2-morpholinol as a white solid. This was used without further purification for the chiral chromatography described below.

The (+) and (−) enantiomers of (+/−)-(2R*,3R*)-2-(3-chlorophenyl)-3,5,5-trimethyl-2-morpholinol may be separated by the following process. (+/−)-(2R*,3R*)-2-(3-chlorophenyl)-3,5,5-trimethyl-2-morpholinol (2.54 gms.) was dissolved in 250 ml of 2:8 Isopropyl alcohol:Hexane (both HPLC grade). A Daicel Chiralcel OD column (2×25 cm.) was equilibrated for one hour at 8 ml./min.in the elution solvent, 1:9:0.2 Isopropanol:Hexane:Diethylamine. The solution of the (+/−)-(2R*,3R*)-2-(3-chlorophenyl)-3,5,5-trimethyl-2-morpholinol was injected in 1 ml. aliquots by an automated Waters Prep LC 2000, using a Waters 510 EF pump for injections. Each run was 15 minutes in length, using the conditions listed before. The separated optical isomers were collected by fraction collector (Waters) at a 2% above baseline threshold, based on 2 absorbance units full scale at 240 nm (Waters 490E UV detector). Each optical isomer solution was evaporated on a rotary evaporator at 40 degrees Centigrade and aspirator vacuum. After drying for 6 hours under high vacuum at room temperature, optical isomer 1 weighed 1.25 gm. and optical isomer 2 weighed 1.26 gm.

The enantiomeric purity of each isomer was assayed by analytical chiral HPLC on a Waters 860 HPLC with 996 Photodiode Array detector, using a Daicel Chiralcel OD-H column (4.6×250 mm.) eluted with 1:9:0.2 Isopropyl alcohol:Hexane:Diethylamine at 1 ml/min. Optical isomer 1 was 100% pure (R.T. 6.117 min.). Optical isomer 2 was 99.19% pure (R.T. 6.800 min.), containing 0.81% optical isomer 1 (R.T. 6.133 min.).

Hydrochloride salts of the separated enantiomers were obtained by the following processes. 1.25 g (0.005 mol) of optical isomer 1 (retention time 6.117 min) ((−)-(2R,3R)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.32 g (90%) of (−)-(2R,3R)-2-(3-chlorophenyl)-3,5,5-trimethyl-2-morpholinol hydrochloride as a white solid: mp 208–209° C. NMR (300 Mhz, DMSO-d$_6$); δ 9.72 (br, 1H), 8.76 (br, 1H), 7.54–7.41 (m, 5H), 3.98 (d, 1H), 3.52 (d, 1H), 3.37 (br s, 1H), 1.53 (s, 3H), 1.29 (s, 3H), 0.97 (d, 3H). Anal. Calcd for C$_{13}$H$_{19}$Cl$_2$NO$_2$: C, 53.43; H, 6.55; N, 4.79. Found: C, 53.35; H, 6.57; N, 4.71. $(\alpha)_D^{20°\,C.}$=−33.2° (0.67, 95% EtOH)

1.26 g (0.005 mol) of optical isomer 2 (retention time 6.800 min) (+)-(2S,3S)-2-(3-chlorophenyl)-3,5,5-trimethyl-2-morpholinol) was dissolved in diethyl ether. The solution was filtered and the filtrate was chilled in an ice-bath adding ethereal hydrogen chloride until the solution was acidic. After standing at ambient temperature for 24 h, the resulting solid was filtered, washed with diethyl ether and dried in a vacuum oven at 60° C. for 18 h to give 1.36 g (93%) of (+)-(2S,3S)-2-(3-chlorophenyl)-3,5,5-trimethyl-2-morpholinol hydrochloride as a white solid: mp 208–209° C. NMR (300 Mhz, DMSO-d$_6$); δ 9.87 (br, 1H), 8.76 (br, 1H), 7.54–7.41 (m, 5H), 3.99 (d, 1H), 3.51 (d, 1H), 3.37 (br s, 1H), 1.54 (s, 3H), 1.30 (s, 3H), 0.98 (d, 3H). Anal. Calcd for C$_{13}$H$_{19}$Cl$_2$NO$_2$: C, 53.43; H, 6.55; N, 4.79. Found: C, 53.51; H, 6.58; N, 4.73. $(\alpha)_D^{20°\,C.}$=+31.9° (0.64, 95% EtOH)

The absolute configuration of (+)-(2S,3S)-2-(3-chlorophenyl)-3,5,5-trimethyl-2-morpholinol was determined by the following x-ray crystallographic method. Crystal Data: C$_{13}$H$_{18}$Cl$_2$NO$_2$, M=291, Orthorhombic, space group P2$_1$2$_1$2$_1$, a=8.7348 (6), b=14.9824 (10), c=23.1605 (15) Å, V=3031 (4) Å$^3$, Z=8, Dc=1.276 Mgm$^{-3}$, F(000)=1226.95. Of 12224 reflections measured. 3764 were unique and 2318 which had I>3.0σ(I) were used in subsequent calculations. Data was collected on a Siemens SMART diffractometer using omega scans and monochromated MoKα radiation (λ=0.71073 Å). The positions of all non-hydrogen atoms were determined by direct methods and refined anisotropically. The hydrogen positions were all located in difference syntheses and included in subsequent refinement cycles using a riding model and an idealized bond length of 0.96 Å. The absolute configuration was determined by refinement of the Rogers' parameter and confirmed by an analysis of the 185 best Bijvoet intensity differences which indicated a probability of 0.006 that the model was in error. Least squares refinement minimized Σw(ΔF)$^2$ with weights based on counter statistics. The final agreement factors were R$_f$=0.064 (0.108 for all data), R$_w$=0.068 (0.081 for all data), and GoF=1.93. References included E. J. Gabe, Y. Le Page, J.-P. Charland, F. L. Lee and P. S. White, Journal of Applied Crystallography, 22, 384–387 (1989) and D. Rogers, Acta Crystallographica, A37, 734–741, 1981.

Dosage and Formulation

The amount of compound of formula (I) required to achieve the desired therapeutic effect will, of course depend on a number of factors, for example, the mode of administration, the recipient and the condition being treated. In general, the daily dose will be in the range of 0.02 to 5.0 mg/kg. More particular ranges include 0.02 to 2.5 mg/kg, 0.02 to 1.0 mg/kg, 0.02 to 0.25 mg/kg, 0.02 to 0.15 mg/kg and 0.02 to 0.07 mg/kg.

The compound of formula (I) may be employed in the treatment of depression, attention deficit hyperactivity disorder (ADHD), obesity, migraine, pain, sexual dysfunction, Parkinson's disease, Alzheimer's disease, addiction to cocaine or nicotine-containing (especially tobacco) products as the compound per se, but is preferably presented with one or more pharmaceutically acceptable carriers, diluents or excipients in the form of a pharmaceutical formulation. The carriers, diluents and exipients must, of course, be acceptable in the sense of being compatible with the other ingredients of the formulation and must not be deleterious to the recipient. The carrier may be a solid or a liquid, or both, and is preferably formulated with the agent as a unit-dose formulation, for example, a tablet.

The formulations include those suitable for oral, rectal, topical, buccal (e.g. sub-lingual) and parenteral (e.g. subcutaneous, intramuscular, intradermal or intravenous) administration.

Formulations suitable for buccal (sub-lingual) administration include lozenges comprising a compound of formula (I) in a flavoured base, usually sucrose and acacia or tragacanth, and pastilles comprising the agent in an inert base such as gelatin and glycerin or sucrose and acacia.

Formulations of the present invention suitable for parenteral administration conveniently comprise sterile aqueous preparations of a compound of formula (I), preferably isotonic with the blood of the intended recipient. These preparations are preferably administered intravenously, although administration may also be effected by means of subcutaneous, intramuscular, or intradermal injection. Such preparations may conveniently be prepared by admixing the agent with water and rendering the resulting solution sterile and isotonic with the blood.

Formulations suitable for rectal administration are preferably presented as unit-dose suppositories. These may be prepared by admixing a compound of formula (I) with one or more conventional solid carriers, for example, cocoa butter, and then shaping the resulting mixture.

Formulations suitable for topical application to the skin preferably take the form of an ointment, cream, lotion, paste, gel, spray, transdermal patch, aerosol, or oil. Carriers which may be used include vaseline, lanolin, polyethylene glycols, alcohols, and combinations of two or more thereof.

It should be understood that in addition to the ingredients particularly mentioned above, the formulations may include other agents conventional in the art having regard to the type of formulation in question.

Biological Activity

Biological activity of the compound of formula (I) was demonstrated by in vitro uptake models, the tetrabenazine-induced behavioural depression model, the MPTP-treatment Parkinson's disease model, the chronic constriction injury mononeuropathy model, and a mouse sexual behaviour model. The racemic morpholinol metabolite, (+/−)-(2R*,3R*)-2-(3-chlorophenyl)-3,5,5-trimethyl-2-morpholinol, is referred to herein as "Racemate". The (−) form of the morpholinol metabolite is (−)-(2R,3R)-2-(3-chlorophenyl)-3,5,5-trimethyl-2-morpholinol or pharmaceutically acceptable salts and solvates thereof and is referred to herein as a compound of formula (II):

In vitro Synaptosomal Uptake Experiments

In vitro uptake was determined, as reported previously, using synaptosomes prepared from rat caudoputamen (for dopamine uptake) and hypothalamus (for NA and serotonin uptake) using [$^3$H]-dopamine, [$^3$H]-NA and [$^3$H]-serotonin as transport substrates, respectively. See Eckhardt, S. B., R. A. Maxwell, and R. M. Ferris, A Structure-Activity Study of the Transport Sites for the Hypothalamic and Striatal Catecholamine Uptake Systems. Similarities and differences. *Molecular Pharmacology*, 21: p. 374–9, 1982.

Synaptosomes for use in obtaining in vitro uptake data were prepared from hypothalamus or striatum by gently homogenizing the tissue in a 0.3 M sucrose/25 mM Tris pH 7.4 buffer containing iproniazid phosphate to inhibit monoamine oxidase. The homogenate was centrifuged at 1100×g at 4° C. for 10 min and the supernatant was used for uptake studies. The supernatant (~1 mg tissue protein) was incubated with Km concentrations of [$^3$H]-noradrenaline, [$^3$H]-dopamine or [$^3$H]-serotonin at 37° C. for 5 minutes in Modified Krebs-Henseleit buffer (118 mM NaCl, 5 mM KCl, 25 mM NaHCO$_3$, 1.2 mM NaH$_2$PO$_4$, 1.2 mM MgSO$_4$, 11 mM Dextrose, 2.5 mM CaCl$_2$) in the absence and presence of drug. Under these conditions uptake was linear with respect to both for substrate and tissue (with <5% total substrate transported). Non-specific uptake was defined as uptake at 0° C. [$^3$H]-substrate, which had been transported into synaptosomes, was separated from free [$^3$H]-substrate by filtration over GF/B filters and washing with cold Krebs-Henseleit buffer. The filters were counted for tritum in a liquid scintillation spectrometer.

The data for in vitro synaptosomal uptake are presented as Table 1. Among the 2 enantiomers of the morpholinol metabolite of bupropion, the (+) enantiomer, the compound of formula (I), inhibited noradrenaline (NA) uptake with an IC$_{50}$ of 2.2 µM. In contrast, the (−) enantiomer was ineffective at a concentration of 30 µM. On dopamine (DA) uptake, the compound of formula (I) had an IC$_{50}$ of ~10 µM while the (−) enantiomer was inactive at 30 µM. Neither compound inhibited serotonin uptake at 30 mM.

For comparison, Wellbutrin® was equipotent for inhibiting DA and noradrenaline uptake with IC$_{50}$ values of 1.9 and 2.2 µM, and did not inhibit serotonin uptake at 30 µM. Imipramine (a non-specific tricyclic antidepressant) inhibited NA uptake and serotonin uptake with IC$_{50}$ values of 0.072 and 0.24 µM, respectively.

The compound of formula (I) was approximately twice as potent as Wellbutrin® as an NA inhibitor but, unlike the latter, was approximately 10-fold less potent as an inhibitor of dopamine uptake. These data are consistent with the observed noradrenergic actions of Wellbutrin® and the racemic morpholinol metabolite of bupropion, (+/−)-(2R*,3R*)-2-(3-chlorophenyl)-3,5,5-trimethyl-2-morpholinol hydrochloride, (306U73) in vivo, at their respective anti-TBZ doses (Cooper, B. R., et al, *Neuropsychopharmacology*, 11: p. 133–41, 1994). Behavioral and electrophysiological data suggest that the effects of Wellbutrin® are mediated by a noradrenergic mechanism (ibid).

Tetrabenazine-Induced Behavioural Depression Experiments

Tetrabenazine(TBZ)-induced behavioural depression was used as an in vivo measure of antidepressant activity. The test has been validated with a wide range of antidepressants, known to act through noradrenergic mechanisms (Cooper B. R. et al, "Animal models used in the prediction of antidepressant effects in man", J. Clin. Psychiatry 44: 63–66, 1983). Moreover, the test was also used to identify Wellbutrin® as an anti-depressant. Briefly, animals were injected with the candidate agent (p.o. or i.p.) 30 minutes before receiving an i.p. injection of tetrabenazine (35 mg/kg, as the HCl salt—prepared fresh for each use). Assessments were performed 30 minutes thereafter and included: locomotor activity (1–4 scale); ptosis (1–4 scale) and body temperature as described previously (Cooper, B. R., J. L. Howard, and F. E. Soroko, Animal models used in prediction of antidepressant effects in man (*Journal of Clinical Psychiatry*, 44: p. 63–6, 1983). In all studies, the scientist performing the assessments was blind to the treatments. All parameters were weighted equally to give a "lumped" score (X) through the following algorithm:

$$X=(1+\text{Ptosis score})/(\text{Activity score}*[\text{Temp,treated}/\text{Temp,control}])$$

Figure 1:
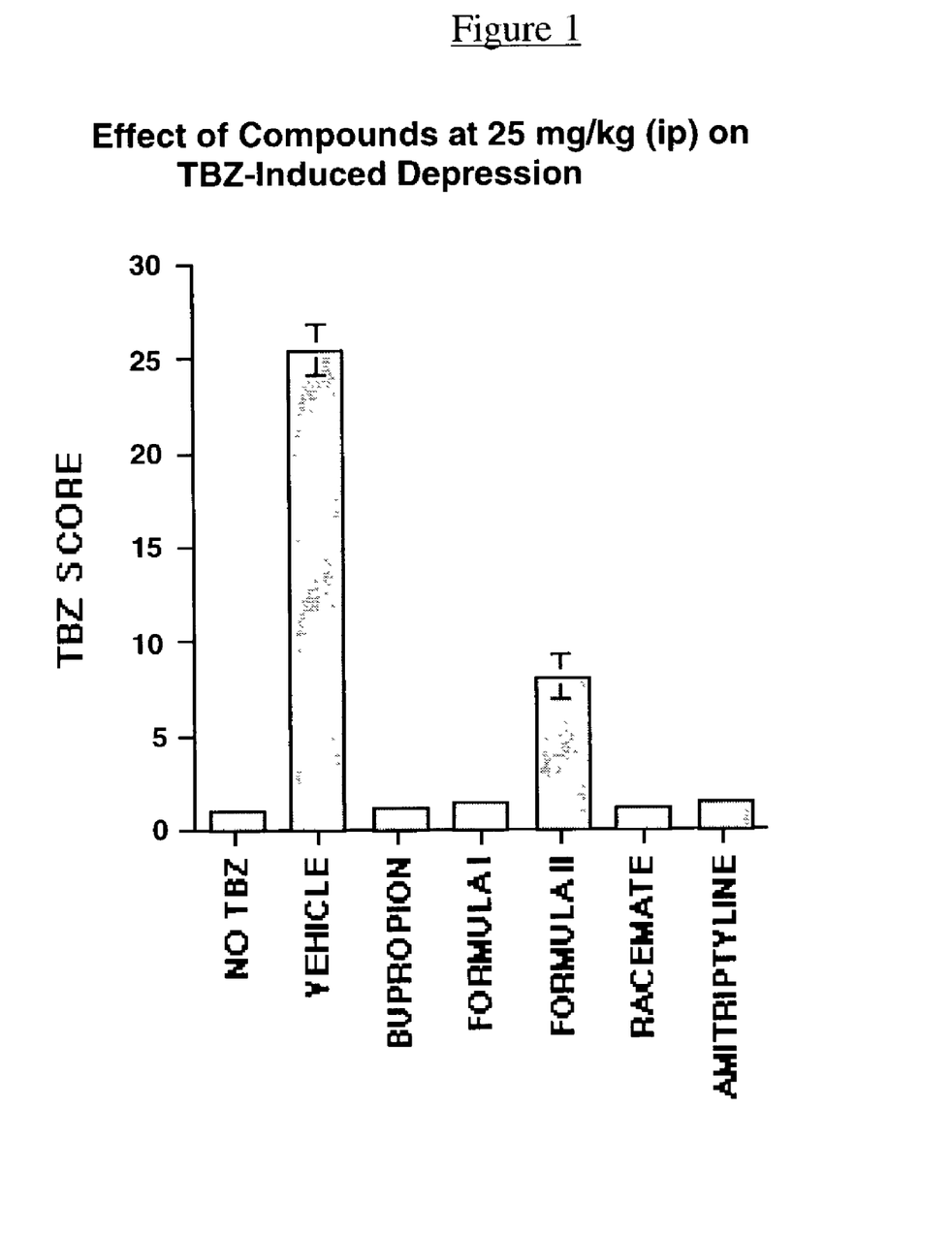
FIG. 1. Effect of Compounds at 25 mg/kg (ip) on TBZ-Induced Depression.

Results from the tetrabenazine-induced behavioural depression model are as follows. Assessed in vivo at 25 mg/kg (ip) the compound of formula (I), the racemate, Wellbutrin® and, for comparison, amitryptyline all abolished the tetrabenazine-induced behavioural depression. In contrast, the (−) enantiomer showed only modest activity (FIG. 1).

Figure 2:
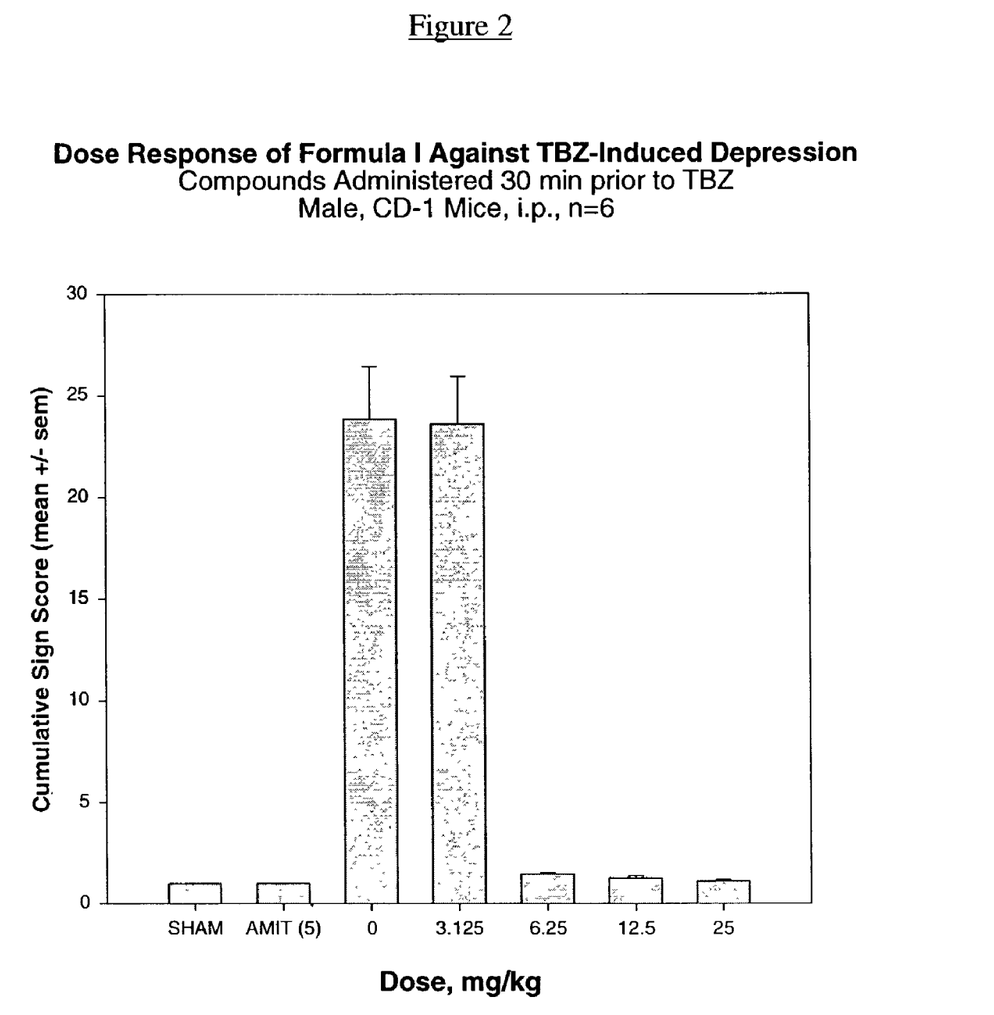
FIG. 2. Dose Response of Compound of Formula I Against TBZ-Induced Depression (Compounds administered 30 minutes prior to TBZ, Male, CD-1 Mice, i.p., n=6).
Figure 3:
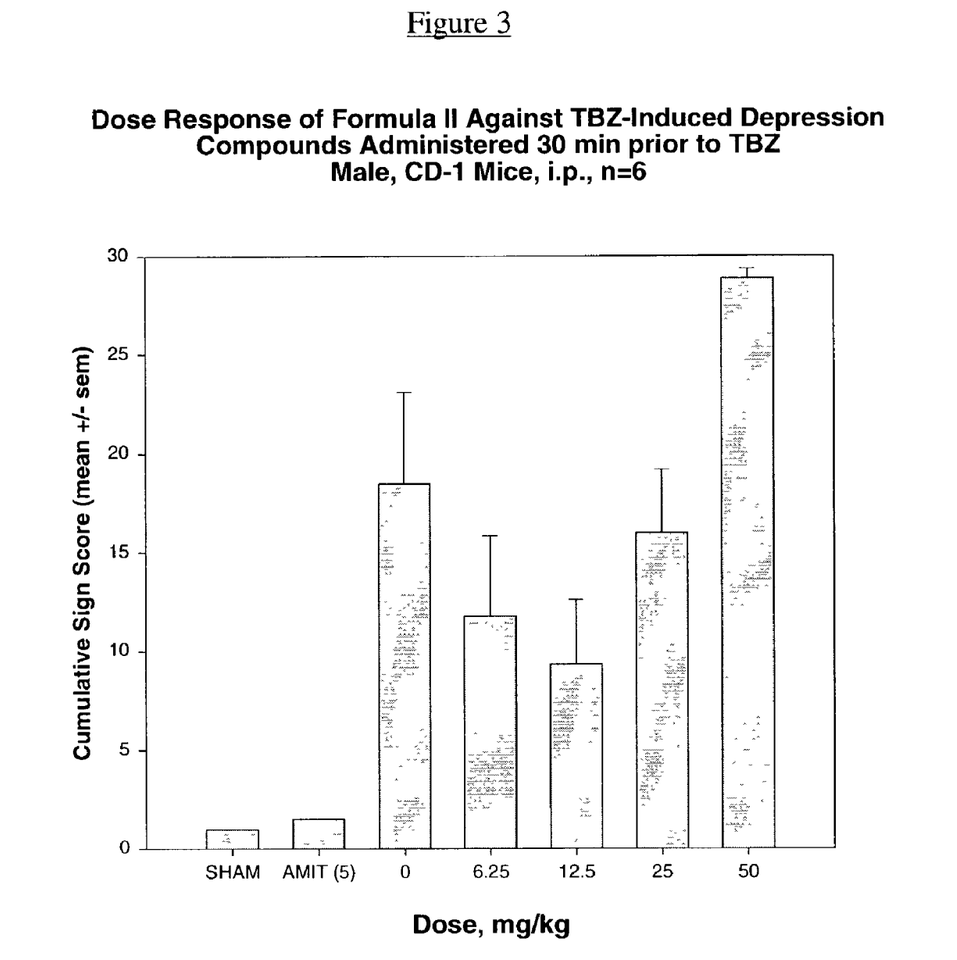
FIG. 3. Dose Response of Compound of Formula II Against TBZ-Induced Depression (Compounds administered 30 minutes prior to TBZ, Male, CD-1 Mice, i.p., n=6).

In the TBZ model of behavioural depression, activity resided in the compound of formula (I). When analysed in a dose-effect study with TBZ, the activity showed a sharp increase in activity between 3 mg/kg and 6 mg/kg (ip) (FIG. 2). The compound of formula II, in comparison, did not possess dose-related activity and, at 50 mg/kg, appeared to worsen the animal's condition (FIG. 3). In FIGS. 2 and 3, AMIT (5) refers to amitryptiline dosed at 5 mg/kg and SHAM refers to a control group of animals that have received no medication at all.

Since the TBZ test has been predictive of anti-depressants acting through noradrenergic mechanisms, and the compound of formula (I) is an inhibitor of noradrenaline uptake and Wellbutrin® is metabolised to this morpholinol in vivo, the data suggest that the anti-depressant activity of Wellbutrin® is likely to result from the effects of the compound of formula (I). (Welch, R. M., A. A. Lai, and D. H. Schroeder, Pharmacological significance of the species differences in bupropion metabolism. *Xenobiotica*, 17: p. 287–98, 1987).

By extension, other activities of Wellbutrin® could be attributed to the compound of formula (I). In particular, a noradrenergic mechanism is common to agents used to treat ADHD (e.g. methylphenidate and amphetamine). While the molecular mechanism for Wellbutrin's effects on smoking cessation is less well understood, a catecholaminergic pathway is thought to participate in the behavioural reinforcing properties of nicotine. Wellbutrin® (and, by extension, the compound of formula (I)), by augmenting NA release into brain synapses, could mimic some of the actions of nicotine and, thus, decrease the signs associated with nicotine withdrawal. Additionally, amphetamines have been used to treat obesity. The addictive properties of amphetamine, however, preclude its use for most obese patients. Wellbutrin® causes weight loss and, like amphetamine, acts through a noradrenergic mechanism. (Zarrindast, M. R. and T. Hosseini-Nia, Anorectic and behavioural effects of bupropion. *General Pharmacology*, 19: p. 201–4, 1988 and Harto-Truax, N., et al., Effects of Bupropion on Body Weight. *Journal of Clinical Psychiatry*, 44: p. 183–6, 1983). However, unlike amphetamine, Wellbutrin® is not addictive. (Lamb, R. J. and R. R. Griffiths, Self-administration in Baboons and the Discriminative Stimulus Effects in Rats of Bupropion, Nomifensine, Diclofensine and Imipramine. *Psychopharmacology*, 102: p. 183–90, 1990; Bergman, J., et al., Effects of Cocaine and Related Drugs in Nonhuman Primates. III. Self-administration by Squirrel Monkeys. *Journal of Pharmacology & Experimental Therapeutics*, 251: p. 150–5, 1989 and Johanson, C. E.; and J. E. Barrett, The Discriminative Stimulus Effects of Cocaine in Pigeons. *Journal of Pharmacology & Experimental Therapeutics*, 267: p. 1–8, 1993). By extension, the compound of formula (I) would also be expected to have efficacy in obesity and cocaine addiction.

Additional studies demonstrating the use of bupropion in the treatment of the conditions referred to above have been published as follows: bipolar depression (*Journal of Affective Disorders*, 56(2–3): p 237–243, December 1999; *J. Clin. Psych.*, 55: p 391–393, 1994), sexual dysfunction (*Journal of Sex and Marital Therapy*, 13(4), p 239–252, 1987), HSDD (*Journal of Sex and Marital Therapy*, 27: p 303–316, 2001), obesity (*Obesity Research*, 9: p 544–551, 2001), treatment of SSRI-induced sexual dysfunction (*J. Clin. Psych.*, 62: p 185–190, 2001; *J. Clin. Psych.*, 54: p 459–465, 1993; *J. Clin. Psych.*, 59: p 112–115, 1998; *Ann. Clin. Psych.*, 9: p 241–245, 1997), neuropathic pain (*Clin. J. Pain*, 16(1): p 6–11, March 2000; *Neurology*, 57, p 1583–1588, 2001).

MPTP-Treatment Parkinson's Disease Model

Figure 4:
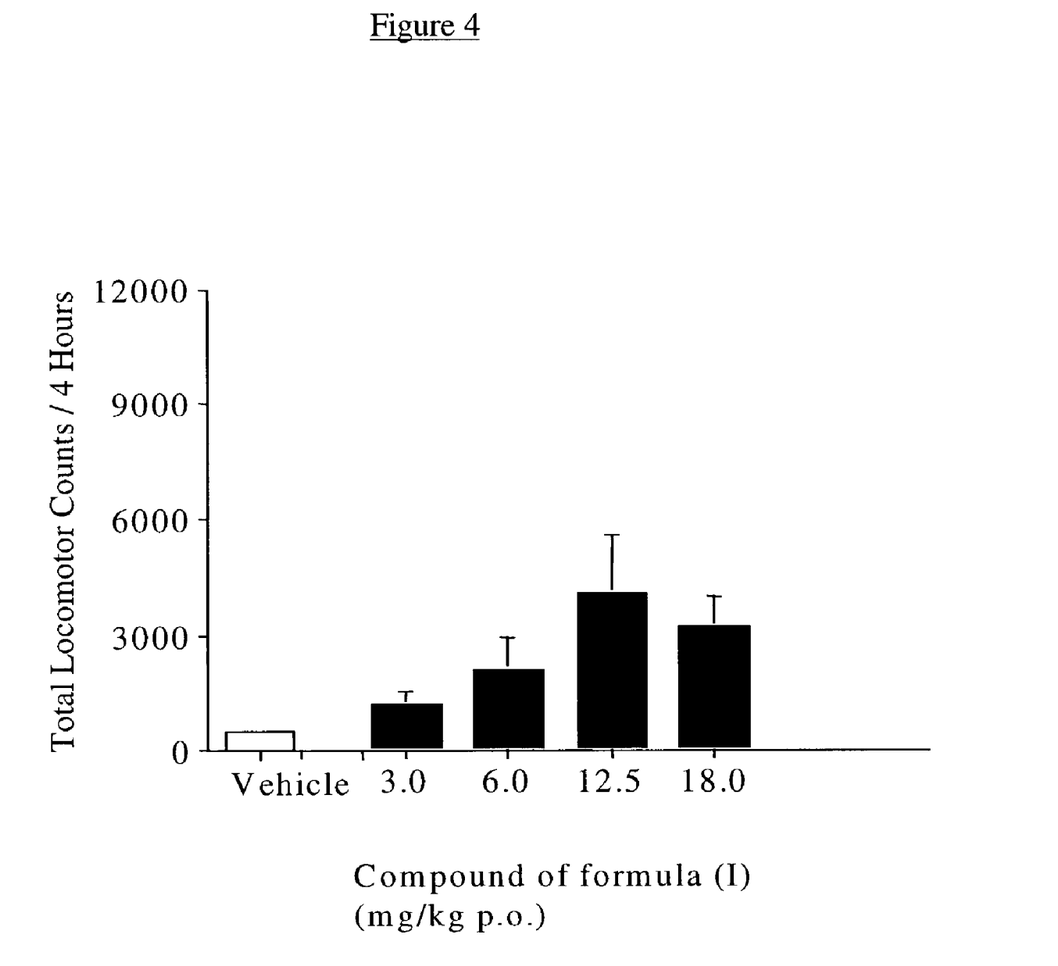
FIG. 4. Effect of Compound of formula (I) on locomotor deficits in MPTP-induced Parkinsonian marmosets.
Figure 5:
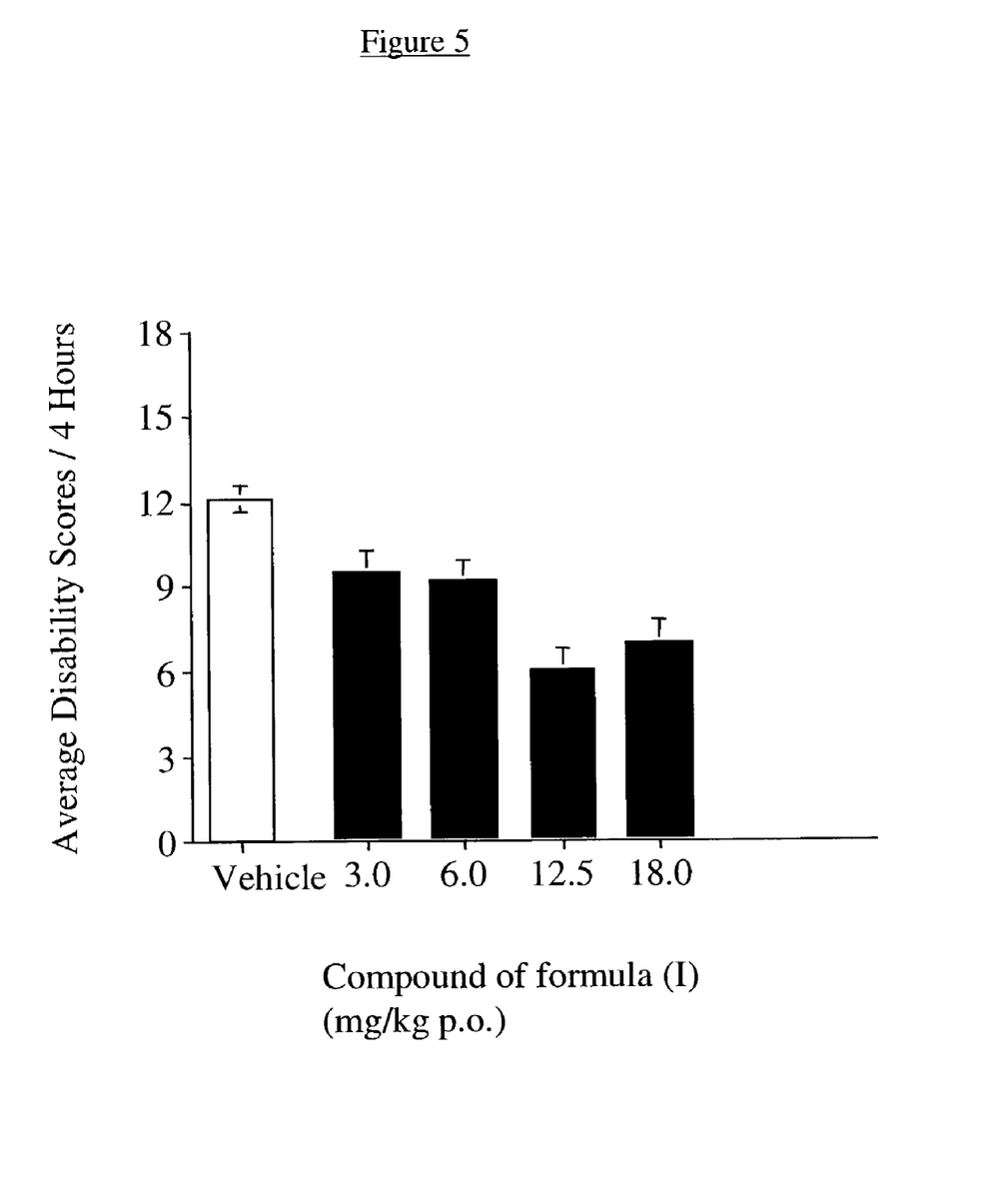
FIG. 5. Effect of Compound of formula (I) on motor disability in MPTP-induced Parkinsonian marmosets.

Locomotor deficits and motor disability were induced in marmosets by the administration of MPTP 2 mg/kg sc on five consecutive days. After the acute effects of MPTP administration had been overcome, bradykinesia, rigidity and loss of vocalisation remained. The compound of formula (I) (as its hydrochloride salt) was administered once weekly by oral gavage, freshly dissolved in 10% sucrose solution with dosages calculated as the free base. Assessment of locomotor activity was by use of automatic locomotor cages (Smith et al., *Movmt. Disord.*, 12: p 935–945, 1997) to monitor climbing, floor and perch activity. Assessment of motor disablities was by an observer through a one-way mirror: alertness, checking movements, posture, balance/coordination, reaction, vocalisation and motility were each scored. A score of zero indicated a "normally" behaing animal, while a maximum total score of 18 in the monitoring period indicated a severely disabled animal. Administration of the compound of formula (I) reversed the locomotor deficits and motor disability exhibited by MPTP-treated marmosets as shown in FIGS. 4 and 5 respectively; data is given as the mean±sem of four animals versus treatment with vehicle alone.

Chronic Constriction Injury Model of Mononeuropathy

Mononeuropathy was reproduced in male Random Hooded rats (180–250 g) using the Chronic Constriction Injury (CCI) model as described by Bennett and Xie (1988). Under Isoflurane anaesthesia, the common left sciatic nerve of the rats was exposed at mid thigh level. Four ligatures of Chromic gut (4.0) were tied loosely around the nerve with a 1 mm spacing between each. The wound was then closed and secured with suture staples. The surgical procedure was identical for the sham operated animals except the sciatic nerve was not ligated. The animals were allowed a period of 12 days to recover from the surgery before any behavioural testing began.

The effect of the compound of formula (I) (administered as the hydrochloride salt at 20 mgkg$^{-1}$ t.i.d. p.o. chronically for a period of 7 days) on CCI-induced decrease in mechanical paw withdrawal threshold was measured using an algesymeter (Randall & Selitto, 1957).

Figure 6:
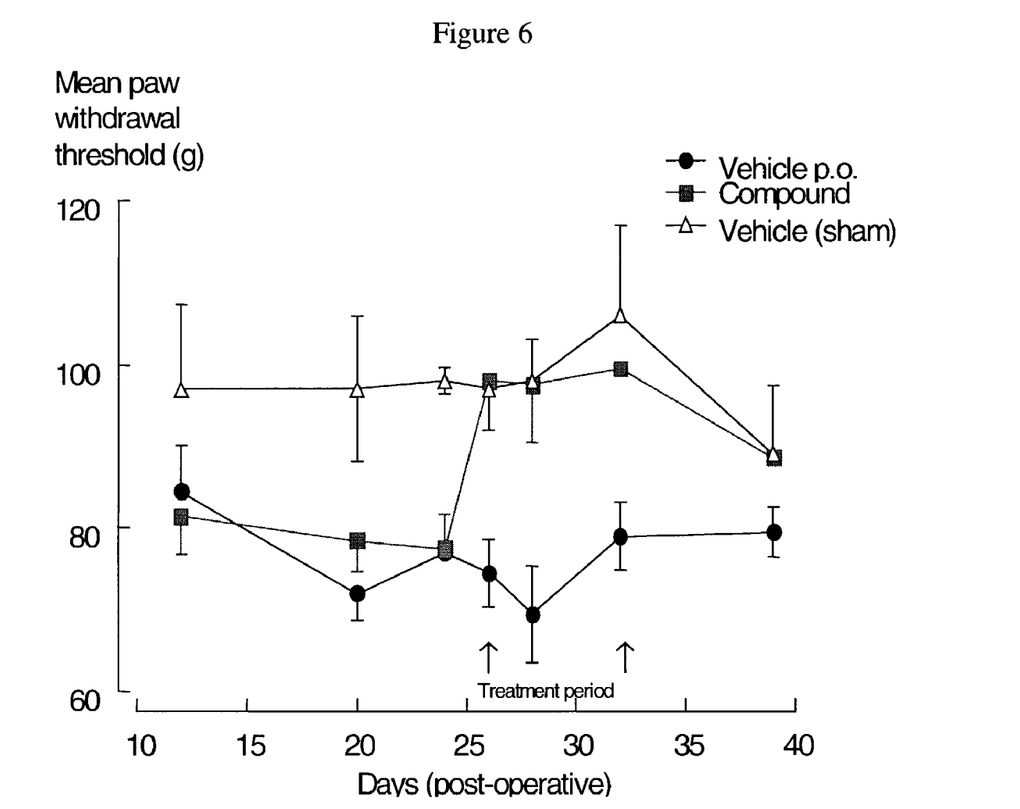
FIG. 6. Effect of Compound of formula (I) on CCI-induced decrease in rat mechanical paw withdrawal threshold.

The data is shown in FIG. 6, expressed as mean ±sem comparing the difference between the drug-treated group and vehicle-treated groups. The CCI operated animals were showing the characteristic decrease in paw withdrawal threshold, demonstrating the onset of neuropathic hypersensitivity, prior to the start of treatment. A single dose of the compound of formula (I) (20 mgkg$^{-1}$) produced an immediate reversal of the fall in paw withdrawal threshold back towards sham operated levels. This reversal was maintained throughout the chronic dosing period, falling back towards CCI-operated vehicle-treated levels on cessation of treatment.

Mouse Sexual Behaviour Model

Male (10 weeks old) and female (8 weeks old) mice (C57BL/6 inbred strain, Charles River, Como (Italy) that had no reproductive or copulatory experience were used in the study. Females were brought into behavioral oestrus with s.c. injections of 0.03 mg estradiol benzoate approximately 48 hr before testing and 0.1 mg progesterone, in sesame oil, 4 hr before testing.

The compound of formula (I) (as its hydrochloride salt) was dissolved in saline to provide a solution for intraperitoneal injection at a dose of 3 mg/kg, with a dose volume of 10 ml/kg. Dosing was performed one hour prior to the test.

Tests were conducted in Perspex arenas, 30 cm in diameter and 50 cm high, which were placed in the cage in which males had been placed individually one day prior to test. The sexual behaviour was filmed remotely under red light for 30 min using a video camera and recorder, the test starting immediately after placing a female mouse into the male's cage. Behavior parameters recorded were (i) the extent of male/female interaction, (ii) the extent of genital sniffing, and (iii) the mount frequency (the number of male mounts).

The results are set out in Tables 2 to 4 below. The compound of formula (I) (as its hydrochloride salt) administered by intraperitoneal injection caused a statistically significant (unpaired t-test) increase in male/female interaction and genital sniffing, and a trend towards increasing mount frequency.

Safety and Toxicity

Additional dose-ranging studies were performed to determine the range of safe doses for the isomers and the racemate. Animals were observed for the presence of serious adverse events (e.g. seizures and deaths) following administration of the compounds of formula I, formula II or the racemate by the oral and intraperitoneal (i.p.) routes. The data are presented as Table 5.

Administered orally, at 100 mg/kg p.o., seizures were observed with the compound of formula II and the racemate but not with the compound of formula I. Seizures were observed in all of the animals with all 3 compounds when dosed at 300 mg/kg. Additionally, the 300 mg/kg oral dose resulted in 100 and 80% lethality for the compound of formula II and the racemate while no deaths were observed with the compound of formula I.

Administered i.p., all of the compounds produced seizures at 100 mg/kg. No deaths were observed with the compound of formula I whereas the compound of formula II and the racemate resulted in lethality of 100% and 20%, respectively. At the 300 mg/kg oral dose all of the lethality was observed for all of the compounds.

TABLE 1

Effects on Uptake In Vitro

| Compound | IC50 (µM) | SEM |
|---|---|---|
| [$^3$H]-Dopamine Uptake | | |
| Bupropion | 1.9 | 0.15 |
| Formula (I) | 9.3 | 0.41 |
| Formula (II) | >100 | |
| [$^3$H]-Noradrenaline Uptake | | |
| Bupropion | 2.2 | 0.7 |
| Formula (I) | 1.1 | 0.07 |
| Formula (II) | >30 | |
| Imipramine | 0.072 | 0.020 |
| [$^3$H]-Serotonin Uptake | | |
| Bupropion | >30 | |
| Formula (I) | >30 | |
| Formula (II) | >100 | |
| Imipramine | 0.24 | 0.03 |

TABLE 3

Male/Female interaction

| Treatment | M/F interaction (sec) |
|---|---|
| Control | 110.4 ± 8.8 |
| Compound of formula (I) | *228.8 ± 30.3 |

*P < 0.05, unpaired t-test

TABLE 4

Genital sniffing

| Treatment | Time spent in genital sniffing (sec) |
|---|---|
| Control | 94.2 ± 10.8 |
| Compound of formula (I) | *203.6 ± 30.1 |

*P < 0.05, unpaired t-test

TABLE 5

Mount frequency

| Treatment | No. of events ± SEM |
|---|---|
| Control | 2.1 ± 0.7 |
| Compound of formula (I) | 6.6 ± 1.7 |

TABLE 6

Adverse Events Associated with Compounds of Formula I, Formula II and the Racemate

| Compound | Route | Dose (mg/kg) | Seizures (%) | Time to Seizures (min) | % Died | Time to Death (min) |
|---|---|---|---|---|---|---|
| Formula I | i.p. | 100 | 100 | 3.93 | 0 | n/a |
| Formula I | p.o. | 100 | 0 | n/a | 0 | n/a |
| Formula I | i.p. | 300 | 100 | 3.95 | 100 | 6 |
| Formula I | p.o. | 300 | 100 | 11.23 | 0 | n/a |
| Formula II | i.p. | 100 | 20 | 5 | 100 | 7 |
| Formula II | p.o. | 100 | 100 | 7.2 | 0 | n/a |
| Formula II | i.p. | 300 | 100 | 1.1 | 100 | 6 |
| Formula II | p.o. | 300 | 100 | 6.8 | 100 | 7 |
| Racemate | i.p. | 100 | 100 | 3 | 20 | 14 |
| Racemate | p.o. | 100 | 100 | 9.2 | 0 | n/a |
| Racemate | i.p. | 300 | 100 | 3 | 100 | 3 |
| Racemate | p.o. | 300 | 100 | 6.8 | 80 | 7 | n/a denotes that the effect was not observed and, therefore, no percentage was given.

The invention claimed is:

1. A method of treating depression in a mammal comprising the administration to said mammal of an effective amount of (+)-(2S,3S)-2-(3-chlorophenyl)-3,5,5-trimethyl-2-morpholinol or pharmaceutically acceptable salts and solvates thereof.

2. A method as claimed in claim 1 wherein the treatment is of major depression.

3. A method as claimed in claim 1 wherein the treatment is of bipolar depression.

4. A method as claimed in claim 1 comprising the administration of the compound (+)-(2S,3S)-2-(3-chlorophenyl)-3,5,5-trimethyl-2-morpholinol hydrochloride.

5. A method as claimed in claim 4 wherein said compound has an optical rotation $[\alpha]^{20}_D$ at c=0.64 in 95% EtOH of +31.9°.

* * * * *